United States Patent
Yu

(10) Patent No.: US 11,439,350 B2
(45) Date of Patent: Sep. 13, 2022

(54) DETACHABLE PHYSIOLOGICAL MONITORING DEVICE

(71) Applicant: INDUSTRIAL TECHNOLOGY RESEARCH INSTITUTE, Hsinchu (TW)

(72) Inventor: Yi-Hsin Yu, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 493 days.

(21) Appl. No.: 16/728,369

(22) Filed: Dec. 27, 2019

(65) Prior Publication Data

US 2021/0196198 A1 Jul. 1, 2021

(51) Int. Cl.
| | |
|---|---|
| *A44B 17/00* | (2006.01) |
| *A61B 5/00* | (2006.01) |
| *H01R 13/627* | (2006.01) |
| *H01R 24/00* | (2011.01) |
| *A61B 5/274* | (2021.01) |
| *H05K 1/18* | (2006.01) |

(52) U.S. Cl.
CPC ............ *A61B 5/6804* (2013.01); *A61B 5/274* (2021.01); *H01R 13/627* (2013.01); *H01R 24/00* (2013.01); *A61B 2560/0443* (2013.01); *H05K 1/184* (2013.01)

(58) Field of Classification Search
CPC ............ H01R 13/6277; H01R 13/6273; A41D 1/005; A44B 17/0023; A44B 17/00064
See application file for complete search history.

(56) References Cited

U.S. PATENT DOCUMENTS

| | | | |
|---|---|---|---|
| 8,061,886 B1 * | 11/2011 | Kraus, Jr. ............ | H01R 25/14 362/147 |
| 8,259,460 B2 | 9/2012 | Bhattacharya et al. | |

(Continued)

FOREIGN PATENT DOCUMENTS

| | | |
|---|---|---|
| CN | 105030219 A | 11/2015 |
| CN | 205625915 U | 10/2016 |

(Continued)

OTHER PUBLICATIONS

Taiwanese Office Action and Search Report for Taiwanese Application No. 108147961, dated Jul. 27, 2020.

*Primary Examiner* — Phuong Chi Thi Nguyen
(74) *Attorney, Agent, or Firm* — Birch, Stewart, Kolasch & Birch, LLP

(57) ABSTRACT

A detachable physiological monitoring device includes a detachable electrode and an electrical coupling unit electrically connected to the detachable electrode. The electrical coupling unit includes a flexible substrate, a fabric, and a conductive wire. The flexible substrate has a first surface and a second surface opposite to the first surface, and the flexible substrate has a first opening. The fabric is disposed at the first surface of the flexible substrate. The fabric includes a second opening corresponding to the first opening and a conductive region surrounding the second opening. The conductive wire has a first terminal and a second terminal opposite to the first terminal, and the first terminal is connected to the conductive region. The detachable electrode contacts the conductive region, and is connected to the conductive wire.

11 Claims, 4 Drawing Sheets

(56) References Cited

U.S. PATENT DOCUMENTS

| | | | |
|---|---|---|---|
| 9,510,649 B1 | 12/2016 | Liu et al. | |
| 9,577,374 B1 * | 2/2017 | Grant | H01R 24/38 |
| 9,627,804 B2 * | 4/2017 | Barth | A41D 1/005 |
| 2018/0184735 A1 | 6/2018 | Longinotti-Buitoni et al. | |
| 2018/0213859 A1 | 8/2018 | Laplante et al. | |
| 2019/0224487 A1 * | 7/2019 | Oskin | A61N 1/3968 |
| 2021/0045640 A1 * | 2/2021 | Poltorak | A61B 5/6847 |

FOREIGN PATENT DOCUMENTS

| | | |
|---|---|---|
| CN | 106606359 A | 5/2017 |
| CN | 107708543 A | 2/2018 |
| TW | M506893 U | 8/2015 |
| TW | I623298 B | 5/2018 |
| TW | 201912106 A | 4/2019 |

* cited by examiner

DETACHABLE PHYSIOLOGICAL MONITORING DEVICE

TECHNICAL FIELD

The disclosure relates to a detachable physiological monitoring device, and more particularly to a detachable physiological monitoring device including a detachable electrode.

BACKGROUND

With the progress of technology, the use of wearable physiological monitoring devices is becoming more and more common. Generally speaking, a physiological monitoring device may include an electrode and an electrical coupling unit. The electrode receives a user's physiological signal and transmits it to the electrical coupling unit. However, if the electrodes cannot be detached when the physiological monitoring device is being cleaned, the long-term abrasion will affect the monitoring results and reduce the device life. If the electrical connection between the electrode and the physiological monitoring device is not good, the monitoring results will also be affected.

Therefore, there is still an urgent need to develop a physiological monitoring device that improves the electrical connection effect between the electrode and the electrical coupling unit.

SUMMARY

According to some embodiments of the present disclosure, a detachable physiological monitoring device is provided. The detachable physiological monitoring device includes a detachable electrode and an electrical coupling unit electrically connected to the detachable electrode. The electrical coupling unit includes a flexible substrate, a fabric, and a conductive wire. The flexible substrate has a first surface and a second surface opposite to the first surface, and the flexible substrate has a first opening. The fabric is disposed at the first surface of the flexible substrate. The fabric includes a second opening corresponding to the first opening and a conductive region surrounding the second opening. The conductive wire has a first terminal and a second terminal opposite to the first terminal, and the first terminal is connected to the conductive region. The detachable electrode contacts the conductive region, and is connected to the conductive wire.

According to some embodiments of the present disclosure, a detachable physiological monitoring device is provided. The detachable physiological monitoring device includes a detachable electrode and an electrical coupling unit electrically connected to the detachable electrode. The electrical coupling unit includes a flexible substrate, a fabric, a fixing element and a conductive wire. The flexible substrate has a first surface and a second surface opposite to the first surface, and the flexible substrate has a first opening. The fabric is disposed on the first surface of the flexible substrate. The fabric includes a second opening corresponding to the first opening and a conductive region surrounding the second opening. The fixing element is disposed at the second surface of the flexible substrate corresponding to the first opening. The conductive wire is electrically connected to the conductive region and the fixing element, wherein the detachable electrode is detachably disposed at the fixing element and is in contact with the conductive region.

A detailed description is given in the following embodiments with reference to the accompanying drawings.

DETAILED DESCRIPTION

Figure 1A:
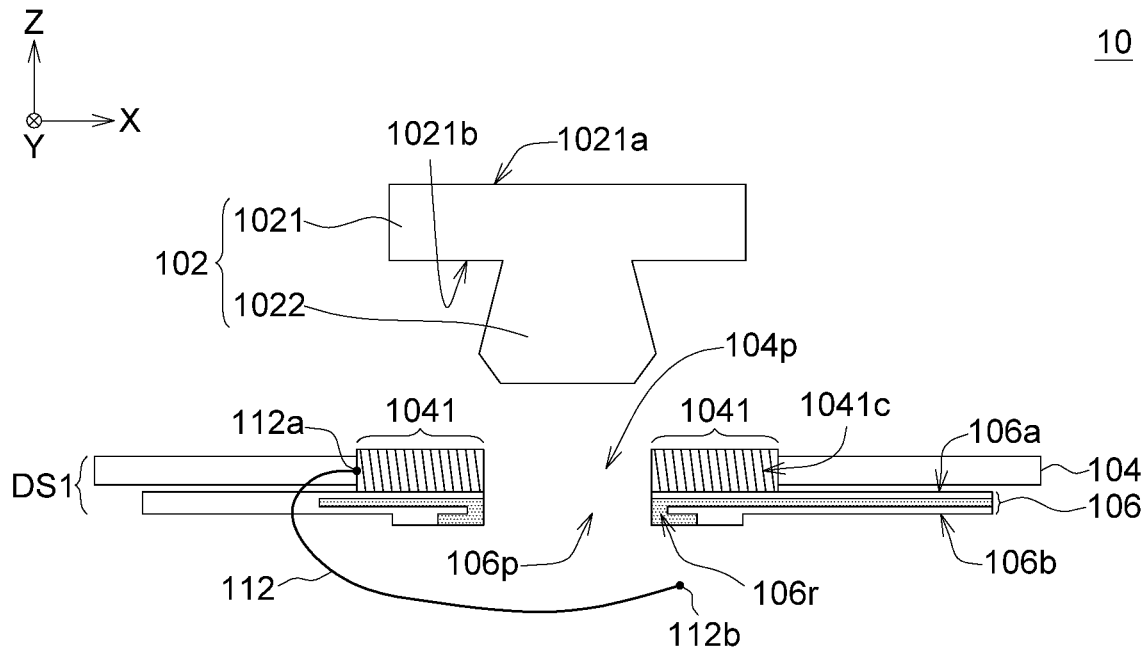
FIG. 1A illustrates a side view of a detachable physiological monitoring device according to an embodiment of the present disclosure in which a detachable electrode and an electrical coupling unit are not connected.

The following is a detailed description of various embodiments, the embodiments are only used as examples, and will not limit the scope of the disclosure to be protected, and portions of the reference numerals of figures in the embodiments are repeated, in order to simplify the description. It does not mean the correlation between different embodiments, and this disclosure can still be implemented with other features, elements, methods and parameters. The provided embodiments are only used to exemplify the technical features of the disclosure, and are not intended to limit the scope of claims of the disclosure. Those with ordinary knowledge in this technical field will be able to make equivalent modifications and variations within the scope of the present disclosure without departing from the spirit of this disclosure according to the following description.

The present disclosure relates to a detachable physiological monitoring device. The detachable physiological monitoring device of the present disclosure includes a detachable electrode and an electrical coupling unit, and the fabric in the electrical coupling unit includes a conductive region. Therefore, compared with the comparative example in which the fabric does not include the conductive region, the conductive region of the present disclosure can be in contact with/connected to the detachable electrode, so that the contact area between the conductive region and the detachable electrode is increased, so the strength of the electrical signal received by the detachable physiological monitoring device can be enhanced. Furthermore, the present disclosure also includes a conductive wire, which can electrically connect the conductive region to the flexible substrate, thereby increasing the transmission path of the electric signal and improving the electrical connection effect between the detachable electrode and the electrical coupling unit.

Figure 1B:
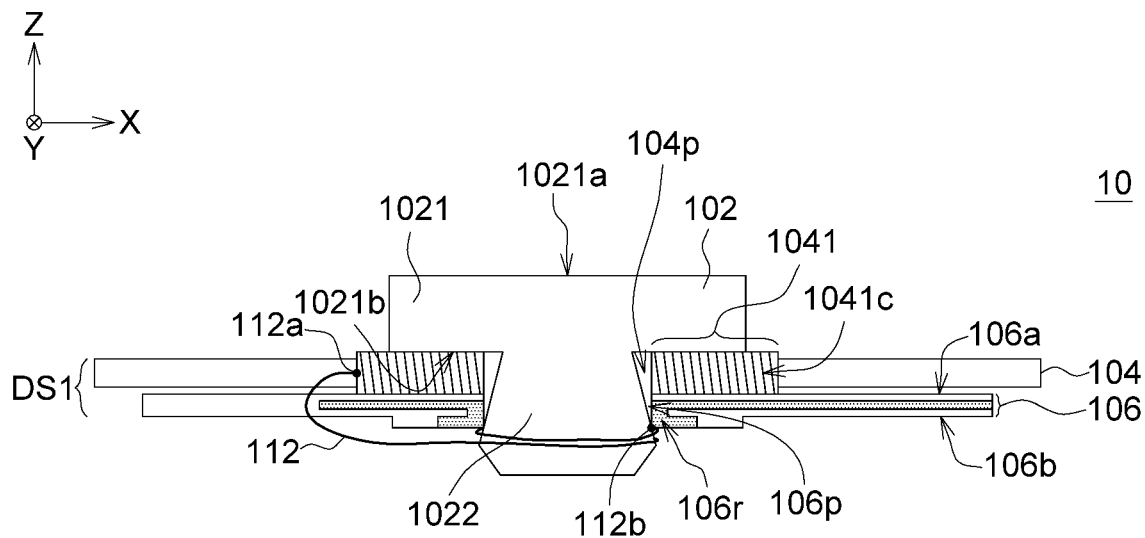
FIG. 1B is a side view of a detachable physiological monitoring device according to an embodiment of the present disclosure in which the detachable electrode and the electrical coupling unit are connected.
Figure 1C:
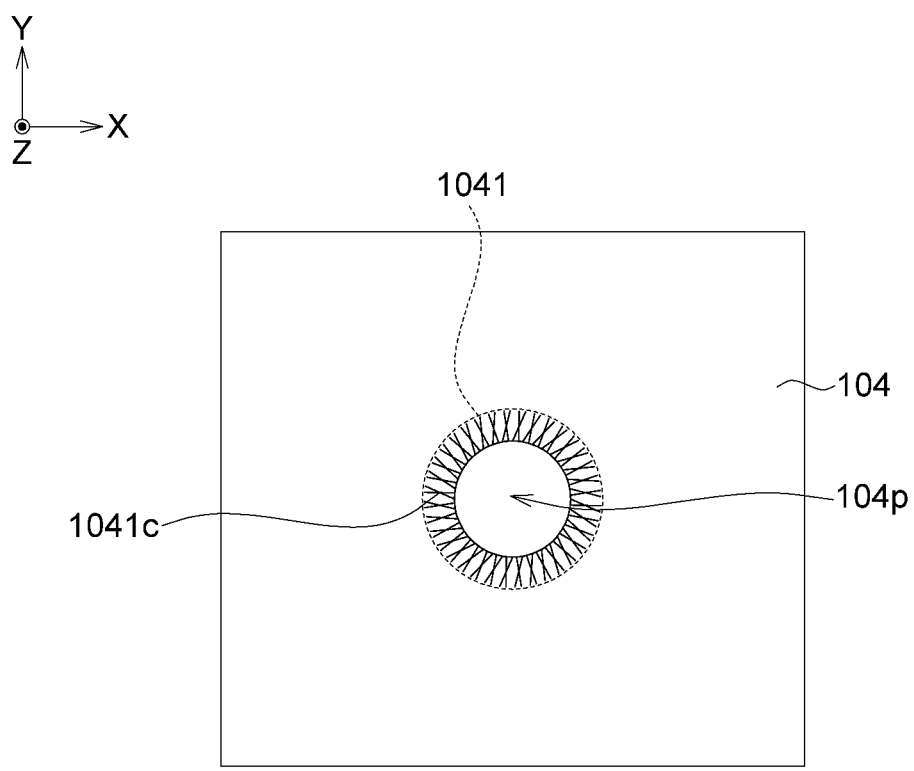
FIG. 1C illustrates a top view of a fabric of a detachable physiological monitoring device according to an embodiment of the present disclosure.

FIG. 1A illustrates a side view of a detachable physiological monitoring device 10 according to an embodiment of the present disclosure in which a detachable electrode 102 and an electrical coupling unit DS1 are not connected. FIG. 1B illustrates a side view of the detachable physiological monitoring device 10 according to an embodiment of the present disclosure in which the detachable electrode 102 and the electrical coupling unit DS1 are connected. FIG. 1O illustrates a top view of a fabric 104 of the detachable physiological monitoring device 10 according to an embodiment of the present disclosure.

Referring to FIGS. 1A and 1B simultaneously. The detachable physiological monitoring device 10 includes a detachable electrode 102 and an electrical coupling unit DS1. When the detachable physiological monitoring device 10 is being cleaned, the detachable electrode 102 can be detached to avoid abrasion of the detachable electrode 102 caused by the cleaning process, so the service life of the detachable physiological monitoring device 10 can be extended.

The electrical coupling unit DS1 includes a flexible substrate 106, a fabric 104, and a conductive wire 112. The flexible substrate 106 has a first surface 106a and a second surface 106b opposite to the first surface 106a, and the flexible substrate 106 has a first opening 106p. In addition, the flexible substrate 106 may include a circuit 106r, and the circuit 106r is adjacent to the first opening 106p. In some embodiments, the circuit 106r can be electrically connected to an electronic device. The flexible substrate 106 is, for example, a flexible printed circuit board or other suitable flexible substrates. The circuit 106r is, for example, a copper foil or other suitable material. The electronic device is, for example, a processor or other suitable electronic device. The fabric 104 is disposed at the first surface 106a, and includes a second opening 104p corresponding to the first opening 106p and a conductive region 1041 (as shown in FIG. 1O) surrounding the second opening 104p. The conductive region 1041 may include one or more conductive yarns 1041c. The conductive yarns 1041c may be distributed in the conductive region 1041 in any manner. For example, the conductive yarn 1041c can be sewn on the fabric in an embroidery manner, but the present disclosure is not limited thereto. By sewing the conductive yarns 1041c around the second opening 104p, it is possible to avoid the situation where the thread of the cloth at the opening is disconnected due to the long-term use of the detachable physiological monitoring device 10. Moreover, compared with the comparative example in which no conductive region is provided around the second opening (that is, no conductive yarn is sewed around the second opening), the contact area with the detachable electrode 102 can be increased due to the conductive region 1041 of the present disclosure and the conductive yarn 1041c included in the conductive region 1041, and the strength of the received signal can be enhanced. In addition, the conductive yarn 1041c can also serve as an elastic buffer around the second opening 104p and reduce contact interference.

Referring to FIG. 1B, the detachable electrode 102 can pass through the first opening 106p and the second opening 104p of the electrical coupling unit DS1 to be physically and electrically connected to (that is, directly contacted) the conductive region 1041 and the flexible substrate 106. In detail, the detachable electrode 102 includes a head portion 1021 and an extending portion 1022 connected to the head portion 1021. The head portion 1021 has an outer surface 1021a and an inner surface 1021b opposite to the outer surface 1021a. In detail, the head portion 1021 of the detachable electrode 102 can directly contact the conductive region 1041, wherein the detachable electrode 102 is in electrical contact with the conductive region 1041 by the inner surface 1021b of the head portion 1021. The extending portion 1022 of the detachable electrode 102 can pass through the first opening 106p and the second opening 104p of the electrical coupling unit DS1 to contact the flexible substrate 106 (for example, directly contact the circuit 106r). The conductive wire 112 has a first terminal 112a and a second terminal 112b opposite to the first terminal 112a. The first terminal 112a is connected to the conductive region 1041. The detachable electrode 102 passes through the first opening 106p and the second opening 104p of the electrical coupling unit DS1 so that the head portion 1021 of the detachable electrode 102 can directly contact the conductive region 1041. The conductive wire 112 can be electrically connected or contacting the extending portion 1022. For example, the conductive wire 112 may be directly wound around the extending portion 1022. In this way, both the detachable electrode 102 and the conductive wire 112 are in electrical contact with the circuit 106r. For another example, the second terminal 112b of the conductive wire 112 may be provided with a clamp (for example, the clamp for clamping the extending portion 1022), which can be electrically connected to the detachable electrode 102 and fixed. In this way, both the detachable electrode 102 and the conductive wire 112 are in electrical contact with the circuit 106r.

In the present embodiment, the shape of the detachable electrode 102 of the present disclosure may be a T shape, but the present disclosure is not limited thereto. In some embodiments, the detachable electrode 102 may be a hard detachable electrode or a soft detachable electrode, and may be formed of a metal, a metal mixture, a mixture of metal and silicone, or other suitable materials. In the present embodiment, the detachable electrode 102 may be a mixture of silver and silicone, but the present disclosure is not limited thereto. The material of the conductive wire 112 may be the same or similar to the conductive yarn 1041c, but the present disclosure is not limited thereto. Compared with the comparative example in which the detachable electrode is a hard detachable electrode, since the detachable electrode 102 according to an embodiment of the present disclosure can be a soft detachable electrode, the user can be more comfortable when wearing the detachable physiological monitoring device 10, and can have less sensation of the foreign objection.

In some embodiments, the outer surface 1021a of the head portion 1021 of the detachable electrode 102 is configured to contact a user's skin to receive a user's physiological signal (electrical signal). The user's physiological signal can be transmitted to the circuit 106r on the flexible substrate 106 through the head portion 1021 and the extending portion 1022 of the detachable electrode 102, and can also be transmitted to the circuit 106r on the flexible substrate 106 through the head portion 1021 of the detachable electrode 102, the conductive region 1041 in the fabric 104 and the conductive wire 112. Compared with a comparative example in which a conductive region is not formed around the second opening and there is no conductive wire connected to the conductive region, the present disclosure not only provides a signal path between the detachable electrode 102 and the flexible substrate 106, but also provides another signal path between the head portion 1021 of the detachable electrode 102, the conductive region 1041, the conductive wire 112 and the flexible substrate 106. Accordingly, the strength of the detected physiological signal can be increased, and the effectiveness of the detachable electrode 102 for measuring the physiological signal can be improved.

Figure 2A:
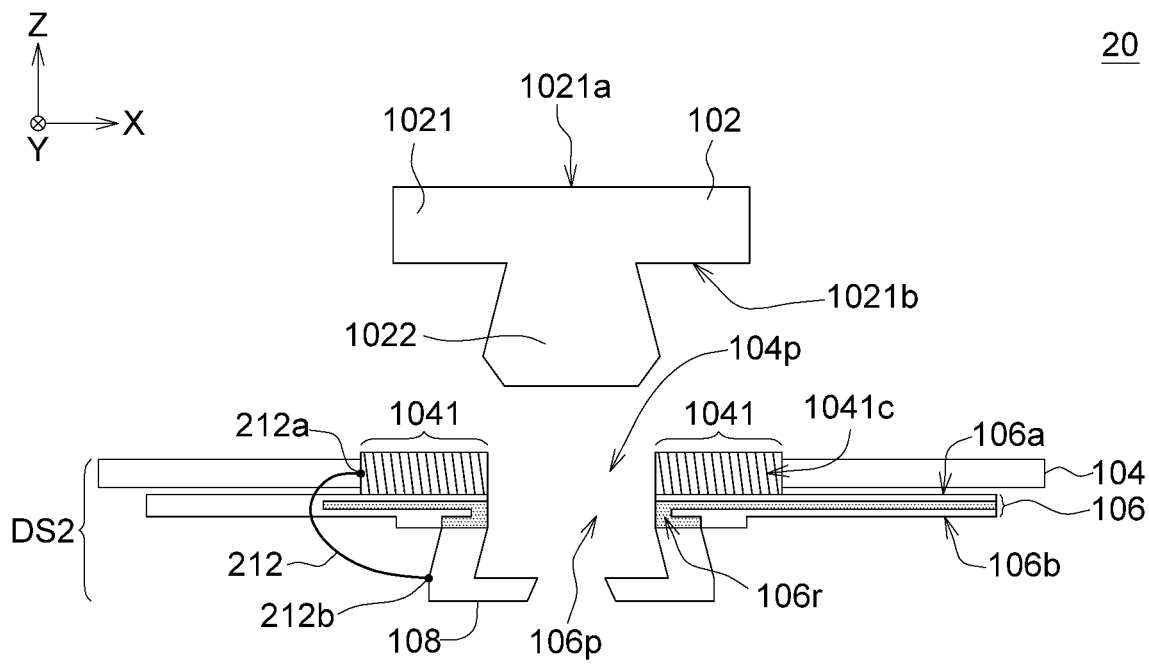
FIG. 2A illustrates a side view of a detachable physiological monitoring device according to another embodiment of the present disclosure in which a detachable electrode and an electrical coupling unit are not connected.
Figure 2B:
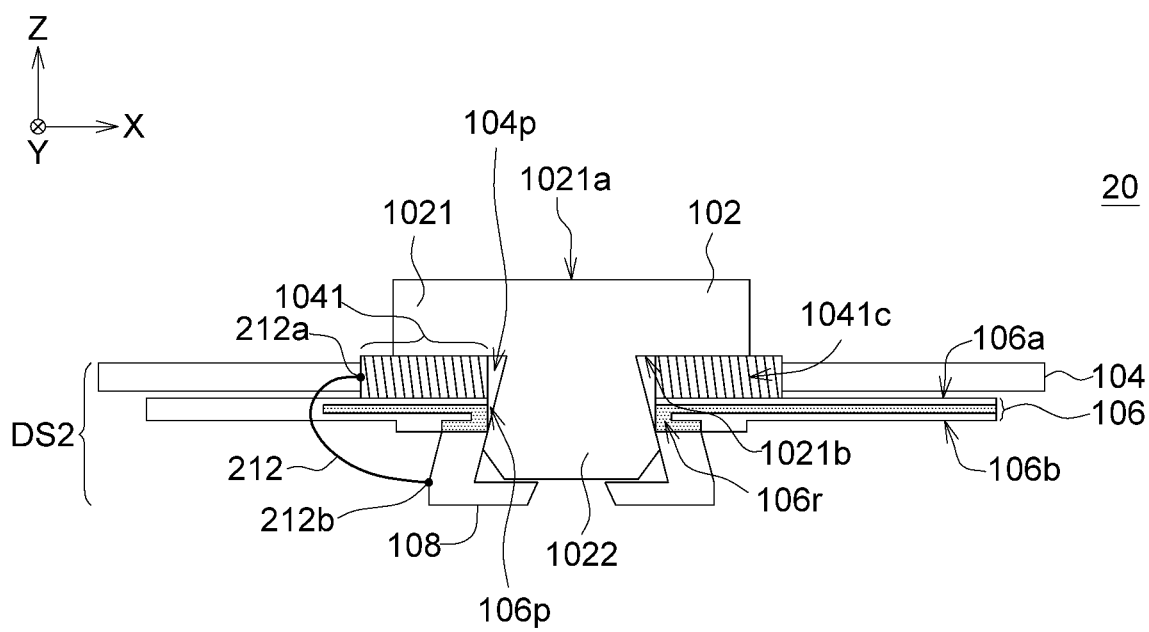
FIG. 2B is a side view of a detachable physiological monitoring device according to another embodiment of the present disclosure in which the detachable electrode and the electrical coupling unit are connected.
Figure 2C:
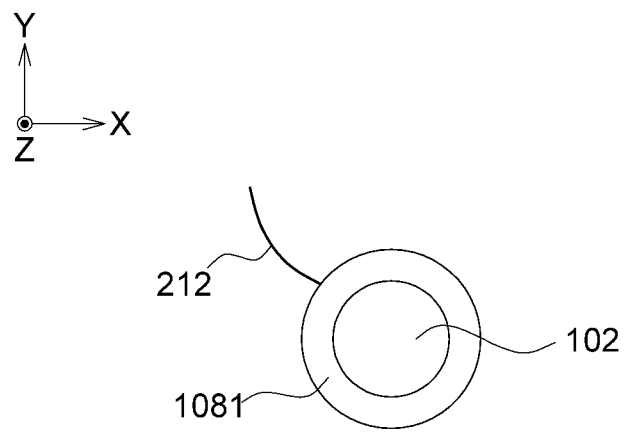
FIG. 2C illustrates a bottom view of a fixing element of a detachable physiological monitoring device according to further embodiment of the present disclosure.
Figure 2D:
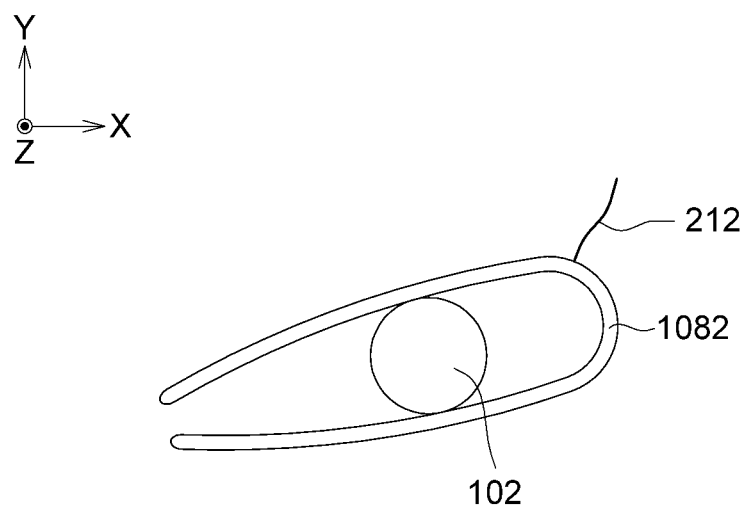
FIG. 2D illustrates a bottom view of a fixing element of a detachable physiological monitoring device according to further embodiment of the present disclosure.

FIG. 2A illustrates a side view of a detachable physiological monitoring device 20 according to another embodiment of the present disclosure in which the detachable electrode 102 and the electrical coupling unit DS2 are not connected. FIG. 2B is a side view of a detachable physiological monitoring device 20 according to another embodiment of the present disclosure in which the detachable electrode 102 and the electrical coupling unit DS2 are connected. FIG. 2C illustrates a bottom view of a fixing element 1081 of the detachable physiological monitoring device 20 according to another embodiment of the present disclosure. FIG. 2D illustrates a bottom view of a fixing element 1082 of the detachable physiological monitoring device 20 according to another embodiment of the present disclosure.

The detachable physiological monitoring device 20 differs from the detachable physiological monitoring device 10 in that it further includes a fixing element 108, and the conductive wire 212 is connected to the fixing element 108. Some components of the detachable physiological monitoring device 20 are the same as or similar to those of the detachable physiological monitoring device 10, and the duplicates will not be described in detail.

Referring to FIGS. 2A and 2B, the fixing element 108 is disposed on the second surface 106b of the flexible substrate 106 corresponding to the first opening 106p. The conductive wire 212 is electrically connected to the conductive region 1041. The conductive wire 212 has a first terminal 212a and a second terminal 212b opposite to the first terminal 212a. The first terminal 212a is connected to the conductive region 1041, and the second terminal 212b of the conductive wire 212 is connected to the fixing element 108. The detachable electrode 102 passes through the first opening 106p and the second opening 104p of the electrical coupling unit DS2, and then inserts into the fixing element 108 so that the detachable electrode 102 contacts the conductive region 1041. In other words, the detachable electrode 102 is detachably disposed at the fixing element 108 of the electrical coupling unit DS2. The extending portion 1022 of the detachable electrode 102 is disposed at the first opening 106p, the second opening 104p, and the fixing element 108, and the head portion 1021 is in contact with the conductive region 1041. The detachable electrode 102 is connected to the fixing element 108 by, for example, the extending portion 1022, so that the detachable electrode 102 can be more stably fixed on the detachable portion DS2. The fixing element 108 is physically or electrically connected to or in contact with the extending portion 1022 of the detachable electrode 102 and the circuit 106r of the flexible substrate 106. The conductive wire 212 is physically and electrically connected to or in contact with the fixing element 108, so that the electrical signal received by the conductive region 1041 can be transmitted to the circuit 106r of the flexible substrate 106 through the conductive wire 212 and the fixing element 108. The fixing element 108 may be formed of a conductive material, such as metal, conductive rubber, or other suitable materials.

In some embodiments, the detachable electrode 102 can be used as a male component, and the fixing element 108 can be used as a female component, so that the detachable electrode 102 extends into the fixing element 108. The fixing element 108 may be an annulus (as shown in FIG. 2C), a clip (as shown in FIG. 2D), or other suitable shaped fixing elements.

Similarly, the user's physiological signal can be transmitted to the circuit 106r on the flexible substrate 106 through the head portion 1021 and the extending portion 1022 of the detachable electrode 102, and can also be transmitted to the circuit 106r on the flexible substrate 106 through the head portion 1021 of the detachable electrode 102, the conductive region 1041 of the fabric 104, the conductive wire 212, and the fixing element 108. Compared with a comparative example in which a conductive region is not formed around the second opening and there is no conductive wire connected to the conductive region, the present disclosure not only provides a signal path between the detachable electrode 102 and the flexible substrate 106, but also provides another signal path between the head portion 1021 of the detachable electrode 102, the conductive region 1041, the conductive wire 212, the fixing element 108 and the flexible substrate 106, so that the strength of the detected physiological signal can be increased, and the effectiveness of the detachable electrode 102 for measuring the physiological signal can be improved.

Referring to Table 1 below, which showed that the resistance values of the detachable physiological monitoring devices of Embodiments 1 to 2 and Comparative Examples 1 to 2 were measured using a multimeter (that is, measuring the resistance between the detachable electrode 102 and the circuits 106r). Embodiment 1 showed a detachable physiological monitoring device 10 as shown in FIGS. 1A and 1B. Embodiment 2 showed a detachable physiological monitoring device 20 as shown in FIGS. 2A and 2B. The detachable physiological monitoring device of Comparative Example 1 was similar to Embodiment 2 except that the conductive region 1041 and the conductive wire 212 were not formed. The detachable physiological monitoring device of Comparative Example 2 was similar to that of Embodiment 2, except that the conductive wire 212 was floating and was not connected to the fixing element 108. The corresponding components in Embodiments 1 to 2 and Comparative Examples 1 to 2 all used the same materials. For example, the detachable electrodes 102 were formed of a mixture of silver and silicone. The circuits 106r were formed of copper foil.

TABLE 1

| detachable physiological monitoring device | Resistance (ohm) |
|---|---|
| Embodiment 1 | 4.4 |
| Embodiment 2 | 4.4 |
| Comparative Example 1 | 20 |
| Comparative Example 2 | 8.5 |

As can be seen from the results in Table 1, in comparison with Comparative Example 1, Comparative Example 2 also had a conductive region including a conductive yarn, so that the contact area between the detachable electrode and the detachable portion was increased, and the resistance may drop from 20 ohms to 8.5 ohms. In comparison with Comparative Example 2, Embodiments 1 and 2 not only had the conductive region 1041 including the conductive yarn 1041c, so that the contact area between the detachable electrode 102 and the detachable portion DS2 can be increased, but also had the conductive wire 1041c of the conductive region 1041 capable of directly or indirectly (through the fixing substrate 108) connecting the circuit 106r of the flexible substrate 106. Therefore, it can provide another signal path for the detachable electrode 102 to be electrically connected to the circuit 106r through the conductive region 1041, so that the resistance value drops to 4.4 ohms. It can be known that the detachable physiological monitoring devices 10 and 20 according to the Embodiments 1 and 2 of the present disclosure can increase the strength of the detected physiological signal and improve the effectiveness of the detachable electrode 102 for measuring the physiological signal.

According to an embodiment of the present disclosure, a detachable physiological monitoring device is provided. The detachable physiological monitoring device includes a detachable electrode and an electrical coupling unit electrically connected to the detachable electrode. The electrical coupling unit includes a flexible substrate, a fabric, and a conductive wire. The flexible substrate has a first surface and a second surface opposite to the first surface, and the flexible substrate has a first opening. The fabric is disposed at the first surface of the flexible substrate. The fabric includes a second opening corresponding to the first opening and a conductive region surrounding the second opening. The conductive wire has a first terminal and a second terminal opposite to the first terminal. The first terminal is connected to the conductive region. The detachable electrode contacts the conductive region and is connected to the conductive wire.

Compared with the comparative example in which no conductive region is provided around the second opening (that is, no conductive yarn is sewed around the second opening), the conductive region in the detachable physiological monitoring device of the present disclosure can increase the contact area between the electrical coupling unit and the detachable electrode, so the strength of the received signal can be enhanced. Furthermore, in addition to providing a signal path between the detachable electrode and the flexible substrate, the detachable physiological monitoring device of the present disclosure also provides another signal path between the head portion of the detachable electrode, the conductive region, the conductive wire and the flexible substrate. Accordingly, the strength of the detected physiological signal can be increased, and the effectiveness of the detachable electrode for measuring the physiological signal can be elevated, and the electrical connection between the detachable electrode and the electrical coupling unit can be improved.

While the disclosure has been described by way of example and in terms of the preferred embodiment(s), it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A detachable physiological monitoring device, comprising:
    a detachable electrode; and
    an electrical coupling unit electrically connected to the detachable electrode, wherein the electrical coupling unit comprises:
        a flexible substrate having a first surface and a second surface opposite to the first surface, and the flexible substrate having a first opening;
        a fabric disposed at the first surface of the flexible substrate, and the fabric comprising: a second opening corresponding to the first opening; and a conductive region surrounding the second opening; and
        a conductive wire having a first terminal and a second terminal opposite to the first terminal, wherein the first terminal is connected to the conductive region,
    wherein the detachable electrode contacts the conductive region, and is connected to the conductive wire.

2. The detachable physiological monitoring device according to claim 1, wherein the detachable electrode comprises a head portion and an extending portion connected to the head portion, and the extending portion passes through the first opening and the second opening, so that the head portion electrically contacts the conductive region, and the conductive wire is connected to the extending portion.

3. The detachable physiological monitoring device according to claim 1, wherein the conductive region comprises a conductive yarn.

4. The detachable physiological monitoring device according to claim 1, wherein the flexible substrate is a flexible printed circuit board.

5. The detachable physiological monitoring device according to claim 1, wherein the conductive wire is wound around the extending portion.

6. The detachable physiological monitoring device according to claim 1, wherein a second terminal of the conductive wire is provided with a clamp for clamping the extending portion.

7. A detachable physiological monitoring device, comprising:
    a detachable electrode; and
    an electrical coupling unit electrically connected to the detachable electrode, wherein the electrical coupling unit comprises:
        a flexible substrate having a first surface and a second surface opposite to the first surface, and the flexible substrate has a first opening;
        a fabric disposed at the first surface of the flexible substrate, and the fabric comprising: a second opening corresponding to the first opening; and a conductive region surrounding the second opening;
        a fixing element disposed at the second surface of the flexible substrate corresponding to the first opening; and
        a conductive wire electrically connected to the conductive region and the fixing element, wherein the detachable electrode is detachably disposed at the fixing element and is in contact with the conductive region.

8. The detachable physiological monitoring device according to claim 7, wherein the detachable electrode comprises a head portion and an extending portion connected to the head portion,
    Wherein the extending portion of the detachable electrode is disposed in the first opening, the second opening and the fixing element, and the head portion contacts the conductive region.

9. The detachable physiological monitoring device according to claim 7, wherein the conductive region comprises a conductive yarn.

10. The detachable physiological monitoring device according to claim 7, wherein the flexible substrate is a flexible printed circuit board.

11. The detachable physiological monitoring device according to claim 7, wherein the fixing element is conductive.

* * * * *